(12) United States Patent
Seo et al.

(10) Patent No.: US 10,675,070 B2
(45) Date of Patent: Jun. 9, 2020

(54) APPARATUS FOR FIXING CERVICAL SPINE

(71) Applicant: CG BIO CO., LTD., Gyeonggi-do (KR)

(72) Inventors: Jun Hyuk Seo, Gyeonggi-do (KR); Dong Ryul Song, Gyeonggi-do (KR); Myoung Lae Jo, Gyeonggi-do (KR); Hae Jun Jeong, Gyeonggi-do (KR); Eugene Yeom, Gyeonggi-do (KR)

(73) Assignee: CG BIO CO., LTD., Gyeonggi-Do (KR)

( * ) Notice: Subject to any disclaimer, the term of this patent is extended or adjusted under 35 U.S.C. 154(b) by 50 days.

(21) Appl. No.: 15/748,256

(22) PCT Filed: Apr. 8, 2016

(86) PCT No.: PCT/KR2016/003677
§ 371 (c)(1),
(2) Date: Feb. 6, 2018

(87) PCT Pub. No.: WO2017/018636
PCT Pub. Date: Feb. 2, 2017

(65) Prior Publication Data
US 2018/0214191 A1 Aug. 2, 2018

(30) Foreign Application Priority Data

Jul. 27, 2015 (KR) .................... 10-2015-0105792
Jul. 27, 2015 (KR) .................... 10-2015-0105794

(51) Int. Cl.
*A61B 17/80* (2006.01)

(52) U.S. Cl.
CPC ...... *A61B 17/8042* (2013.01); *A61B 17/8061* (2013.01)

(58) Field of Classification Search
CPC . A61B 17/80; A61B 17/8023; A61B 17/8028; A61B 17/8033; A61B 17/8042; A61B 17/8061
(Continued)

(56) References Cited

U.S. PATENT DOCUMENTS 6,398,783 B1 * 6/2002 Michelson ......... A61B 17/1604
606/246
6,652,525 B1 * 11/2003 Assaker ............. A61B 17/7059
606/296

(Continued)

FOREIGN PATENT DOCUMENTS

| KR | 10-2011-0021142 | 3/2011 | ............ A61B 17/68 |
| KR | 10-1537062 | 7/2015 | ............ A61B 17/70 |

OTHER PUBLICATIONS

International Search Report from corresponding PCT Application No. PCT/KR2016/003677 dated Jul. 15, 2016, and it's English translation.

*Primary Examiner* — Eric S Gibson
(74) *Attorney, Agent, or Firm* — Harness, Dickey & Pierce, P.L.C.

(57) ABSTRACT

Disclosed are a cervical vertebra fixation device using a plurality of screws characterized by comprising: a body having a length extending across at least two bones and including a first end and a second end opposite to the first end; and three or more openings formed in the body for receiving the plurality of screws, wherein the first end has a profile with at least a portion of the body being removed with respect to the horizontal line perpendicular to the length direction to prevent adjacent segment degeneration, and a cervical vertebra fixation device using at least one screw, comprising: a body fixed into a bone; at least one opening formed in the body for receiving the at least one screw; a cover for preventing any escape of the screws inserted; and (Continued)

a cover screw, wherein the cover is movable with respect to the body to allow the insertion of screws while the cover is coupled to the body.

4 Claims, 14 Drawing Sheets

(58) Field of Classification Search
USPC .................................. 606/70, 71, 280–299
See application file for complete search history.

(56) References Cited

U.S. PATENT DOCUMENTS

| | | | |
|---|---|---|---|
| 7,001,387 B2 | 2/2006 | Farris et al. ..................... 606/69 |
| 7,306,605 B2* | 12/2007 | Ross ................. A61B 17/7059 | 606/70 |
| 7,727,266 B2* | 6/2010 | Lindemann ........ A61B 17/7059 | 606/289 |
| 8,262,705 B2* | 9/2012 | Bray ................. A61B 17/7059 | 606/280 |
| 8,454,667 B2* | 6/2013 | Humphreys ....... A61B 17/8042 | 606/286 |
| 8,556,944 B2* | 10/2013 | Dube ................. A61B 17/1671 | 606/282 |
| 8,702,766 B2* | 4/2014 | Mueller ............. A61B 17/8042 | 606/289 |
| 8,821,554 B2* | 9/2014 | Stanaford .......... A61B 17/7059 | 606/294 |
| 8,840,667 B1 | 9/2014 | Tumialan ................... 623/17.11 |
| 8,906,077 B2* | 12/2014 | Bush, Jr. ............ A61B 17/8042 | 606/296 |
| 8,932,335 B2* | 1/2015 | Humphreys ....... A61B 17/7059 | 606/294 |
| 9,072,548 B2 | 7/2015 | Matityahu ....................... 606/70 |
| D798,455 S* | 9/2017 | Brotman ...................... D24/155 |
| 2002/0120273 A1* | 8/2002 | Needham .......... A61B 17/1728 | 606/281 |
| 2004/0097934 A1* | 5/2004 | Farris ................ A61B 17/7059 | 606/287 |
| 2004/0210217 A1* | 10/2004 | Baynham ............. A61B 17/686 | 606/295 |
| 2004/0220571 A1* | 11/2004 | Assaker ............. A61B 17/7059 | 606/296 |
| 2005/0261689 A1* | 11/2005 | Lin .................... A61B 17/8042 | 606/296 |
| 2007/0123884 A1* | 5/2007 | Abdou ............... A61B 17/8042 | 606/279 |
| 2008/0287999 A1* | 11/2008 | Markworth ........ A61B 17/7059 | 606/280 |
| 2008/0306550 A1* | 12/2008 | Matityahu .......... A61B 17/1728 | 606/290 |
| 2009/0036933 A1* | 2/2009 | Dube ................. A61B 17/1655 | 606/282 |
| 2009/0131988 A1* | 5/2009 | Bush, Jr. ............ A61B 17/8042 | 606/280 |
| 2009/0270927 A1* | 10/2009 | Perrow .............. A61B 17/7059 | 606/286 |
| 2012/0158068 A1* | 6/2012 | Humphreys ....... A61B 17/8042 | 606/286 |
| 2012/0179207 A1* | 7/2012 | Mekhail ............. A61B 17/7059 | 606/281 |
| 2013/0023936 A1* | 1/2013 | Altarac .............. A61B 17/7059 | 606/279 |
| 2014/0066997 A1* | 3/2014 | Humphreys ....... A61B 17/7059 | 606/294 |
| 2015/0080969 A1* | 3/2015 | Holly ................. A61B 17/7059 | 606/286 |
| 2015/0230841 A1* | 8/2015 | Freese ............... A61B 17/8052 | 606/279 |
| 2015/0245859 A1* | 9/2015 | McMillen .......... A61B 17/7059 | 606/289 |
| 2015/0366595 A1* | 12/2015 | Kaufmann ......... A61B 17/8052 | 606/290 |
| 2016/0095637 A1* | 4/2016 | Elsbury ............. A61B 17/7059 | 606/290 |
| 2016/0128738 A1* | 5/2016 | Kim ................... A61B 17/7059 | 606/293 |
| 2018/0214191 A1* | 8/2018 | Seo .................... A61B 17/7059 |

* cited by examiner

Prior Art

APPARATUS FOR FIXING CERVICAL SPINE

CROSS-REFERENCE TO RELATED APPLICATIONS

This application is a national phase application of PCT Application No. PCT/KR2016/003677, filed on 8 Apr. 2016, which claims benefit to Korean Patent Application No. 10-2015-0105792 filed on 27 Jul. 2015 and Korean Patent Application No 1 0-201 5-01 05794 filed on 27 Jul. 2015. The entire disclosure of the applications identified in this paragraph are incorporated herein by reference.

FIELD

The present disclosure relates generally to a cervical vertebra fixation device, and more specifically to a cervical vertebra fixation device which is made easier for inserting and fixing screws, while featuring improved fixation and minimized side effects.

BACKGROUND ART

This section provides background information related to the present disclosure which is not necessarily prior art.

FIG. 1 illustrates an exemplary embodiment of cervical vertebra fixation devices disclosed in KR Patent Official Gazette No. 10-0974498, in which the cervical vertebra fixation device 100 has a body 110 in plate form. A plurality of openings 120; 121, 123, 125 is formed in the body 110, and screws 130 are inserted and guided in these openings 120; 121, 123, 125, respectively, to be fixed to a bone. A resilient cover 150 is used to prevent any escape of the screws 130 inserted. Among other components not yet described, 151 denotes escape-preventing protrusions 151 formed in the resilient cover 150, and 160 denotes windows 160 through which a person can check an insert arranged between adjacent cervical vertebrae. Further, the screw has a body 131, an outer peripheral surface 131a and a thread 131b. 111 denotes the top face of the body of the cervical vertebra fixation device.

DISCLOSURE

Technical Problem

The problems to be solved by the present disclosure will be described in the latter part of the best mode for carrying out the invention.

Technical Solution

This section provides a general summary of the present disclosure and is not a comprehensive disclosure of its full scope or all of its features.

According to one aspect of the present disclosure, there is provided a cervical vertebra fixation device using a plurality of screws, the device comprising: a body having a length extending across at least two bones and including a first end and a second end opposite to the first end; and three or more openings formed in the body for receiving the plurality of screws, wherein the first end has a profile with at least a portion of the body being removed with respect to the horizontal line perpendicular to the length direction to prevent adjacent segment degeneration.

According to another aspect of the present disclosure, there is provided a cervical vertebra fixation device using at least one screw, comprising: a body fixed into a bone; at least one opening formed in the body for receiving the at least one screw; a cover for preventing any escape of the screws inserted; and a cover screw, wherein the cover is movable with respect to the body to allow the insertion of screws while the cover is coupled to the body.

Advantageous Effects

The advantageous effects of the present disclosure will be described in the latter part of the best mode for carrying out the invention.

BEST MODE FOR CARRYING OUT INVENTION

Hereinafter, the present disclosure will now be described in detail with reference to the accompanying drawings.

Figure 1:
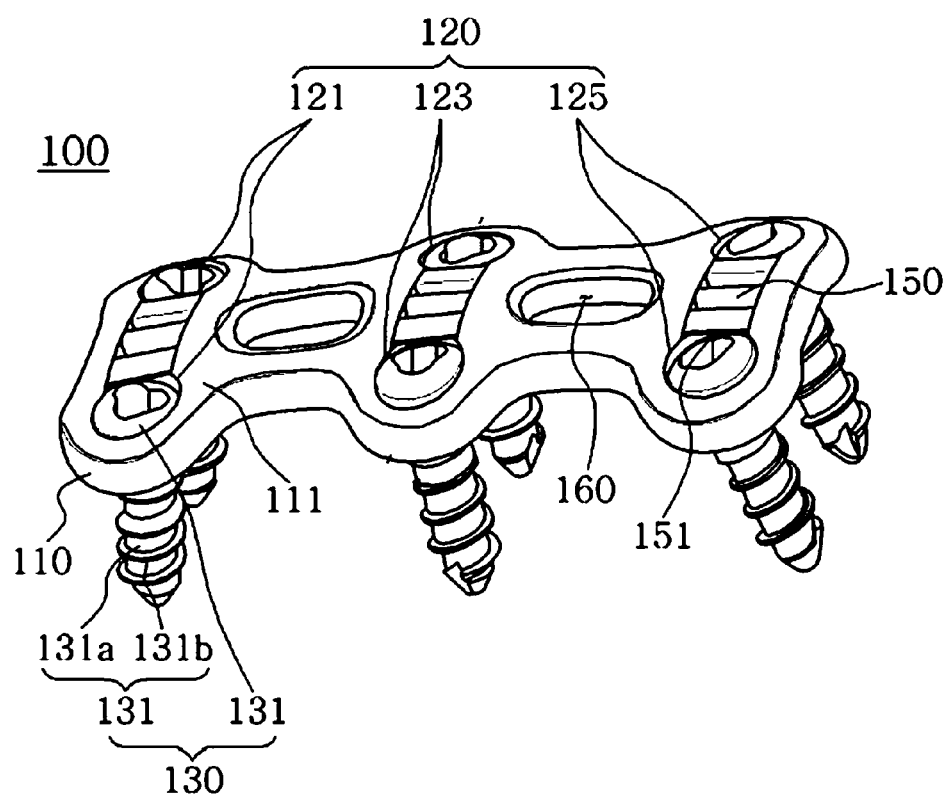
FIG. 1 illustrates an exemplary embodiment of cervical vertebra fixation devices disclosed in KR Patent Official Gazette No. 10-0974498.
Figure 2:
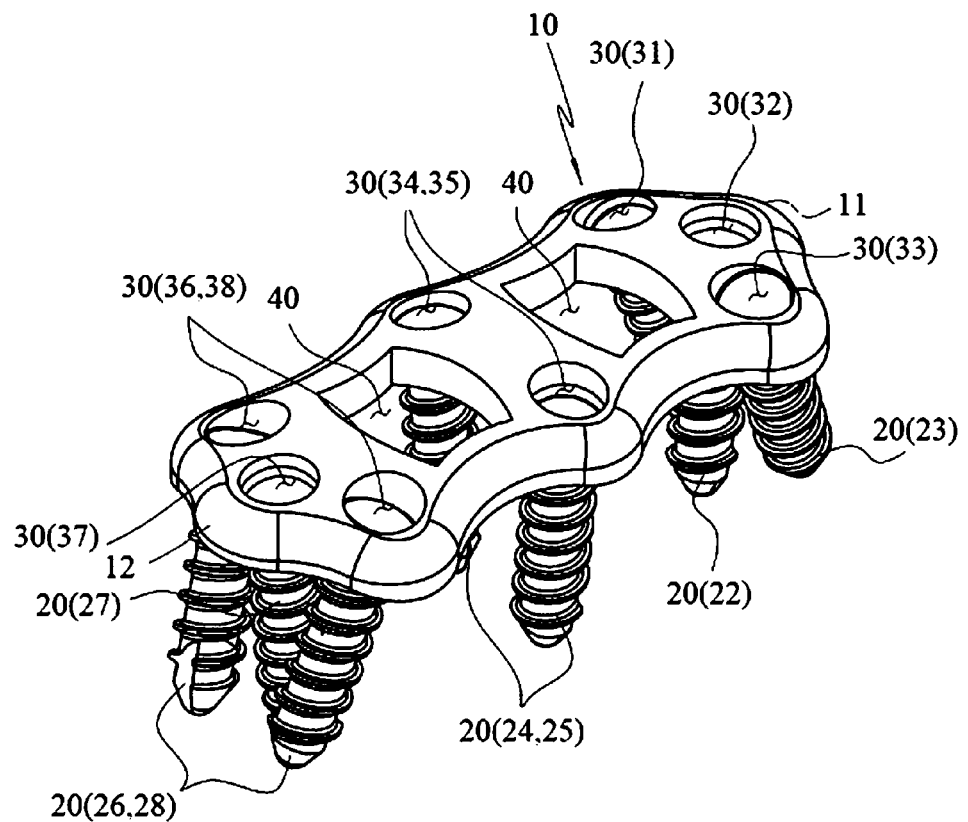
FIG. 2 through FIG. 5 illustrate an exemplary embodiment of the cervical vertebra fixation device according to the present disclosure.
Figure 3:
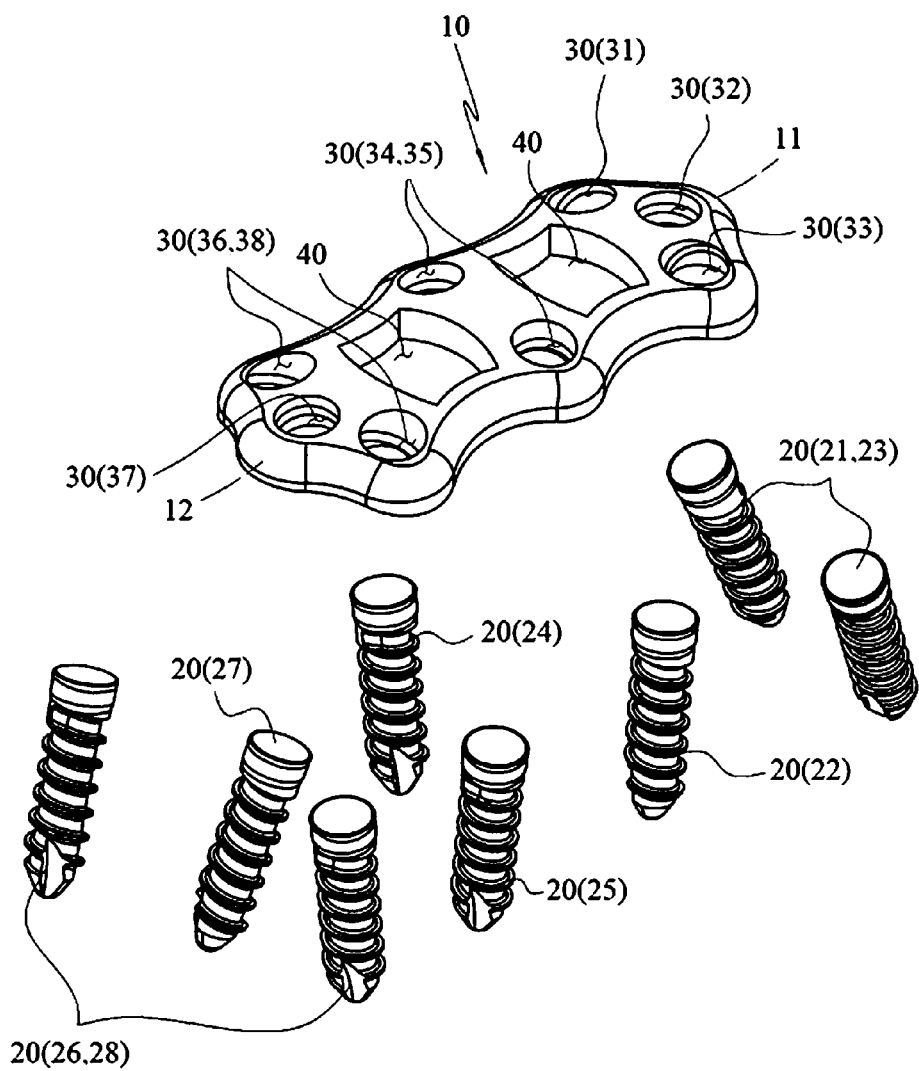
Figure 4:
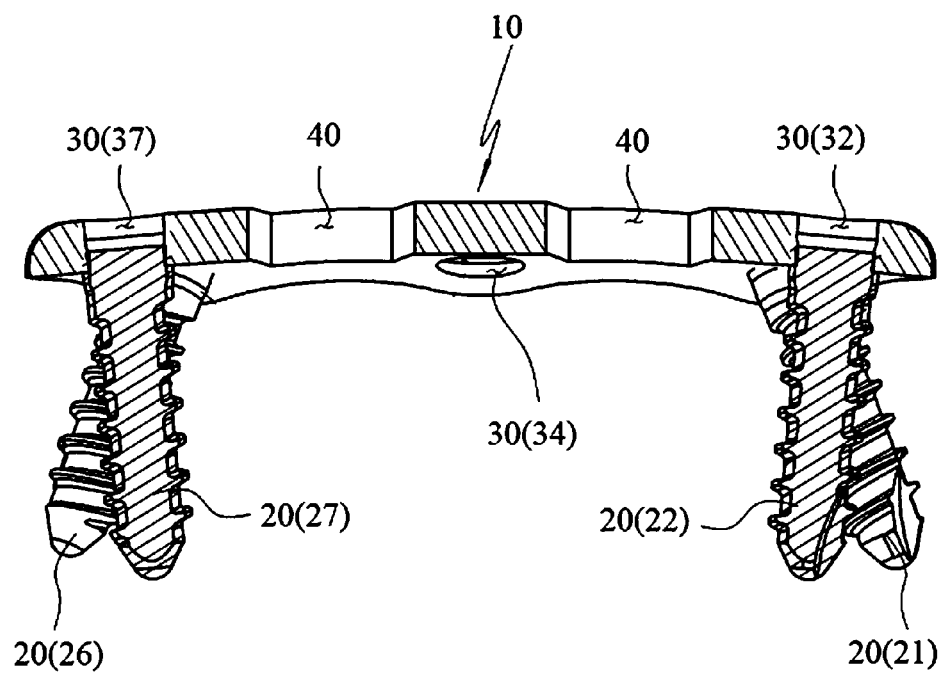
Figure 5:
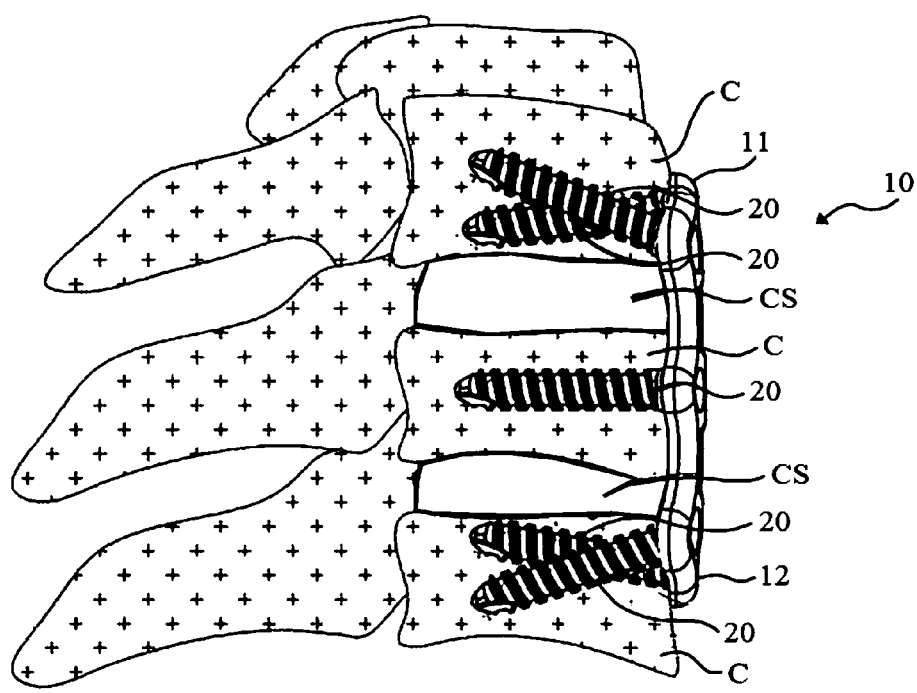

FIG. 2 through FIG. 5 illustrate an exemplary embodiment of the cervical vertebra fixation device according to the present disclosure. The cervical vertebra fixation device has a body 10. As shown in FIG. 5, the body 10 has a length extending across at least two (in this embodiment, three) cervical vertebrae or bones C (CS denotes an insert between cervical vertebrae) and includes a first end 11 and a second end 12 opposite to the first end 11. As can be seen from FIG. 2, the body 10 has a plurality of openings 30; 31, 32, 33, 34, 35, 36, 37, 38 into which a plurality of screws 20; 21, 22, 23, 24, 25, 26, 27, 28 is inserted and guided, respectively. Referring to FIG. 3, in this embodiment, there are three openings 30; 31, 32, 33 on the first end side, and the presence of these three openings 30; 31, 32, 33 can provide an increased fixation force between the bone C and the body 10, as compared with the cervical vertebra fixation device shown in FIG. 1. While this embodiment illustrates a configuration where the opening 32 is located near the first end 11 and the other two openings 31, 33 are located inside the body 10, the invention is not particularly limited thereto as long as the device has three or more openings.

Preferably, at least one of the screws 21, 22, 23 may be inserted into the bone at an angle (obliquely) as shown in FIG. 2 and FIG. 4 so as to increase fixation force between the bone C and the body 10. For example, the screws 21, 23 can be secured into the bone C in the direction facing the screw 22, while the screw 22 can be secured into the bone C in the direction facing the screws 21, 23. The screw 21 and the screw 23 preferably have the same angle, but it is not absolutely required. Still, these screws will be formed in the body 10 in such a manner, if the directions of the screws 21, 22, 23 are determined by the angle or orientation of the openings 31, 32, 33. In an alternate example, as can be seen from FIG. 4, the openings 31, 32, 33 may be formed so that the screw 21, 23 and the screw 22 inserted therein preferably cross each other, substantially increasing the fixation force. A major restriction on the formation of the openings 31, 32, 33 in the body 10 is that the screws 21, 22, 23 should not come out from the bone C through the openings. The screw 22 may be slanted at an angle of about 5 degrees with respect to the face of the opening 32. The screws 21, 23 may be slanted at an angle of 10 to 30 degrees with respect to the faces of the openings 31, 33, and this is a maximum range of angles that would not cause any damage and interference between the bone C into which the screws 21, 23 are inserted and an adjacent bone C. With the screws 21, 22, 23 being arranged at an alternate angle to each other, a high fixation force can be obtained.

Unlike in the cervical vertebra fixation device illustrated in FIG. 1, more portions of the bone C are covered by the first end 11 of the body due to the presence of three or more openings 31, 32, 33 or screws 21, 22, 23 on the side of the first end 11 as shown in FIG. 5, which may result in adjacent segment degeneration (a condition that occurs after anterior arthrodesis, accelerating degeneration of non-fixed adjacent segments (bone)). To resolve this problem, the present disclosure is designed to reduce the coverage of the bone C by the body 10 on the side of the first end 11.

Figure 6:
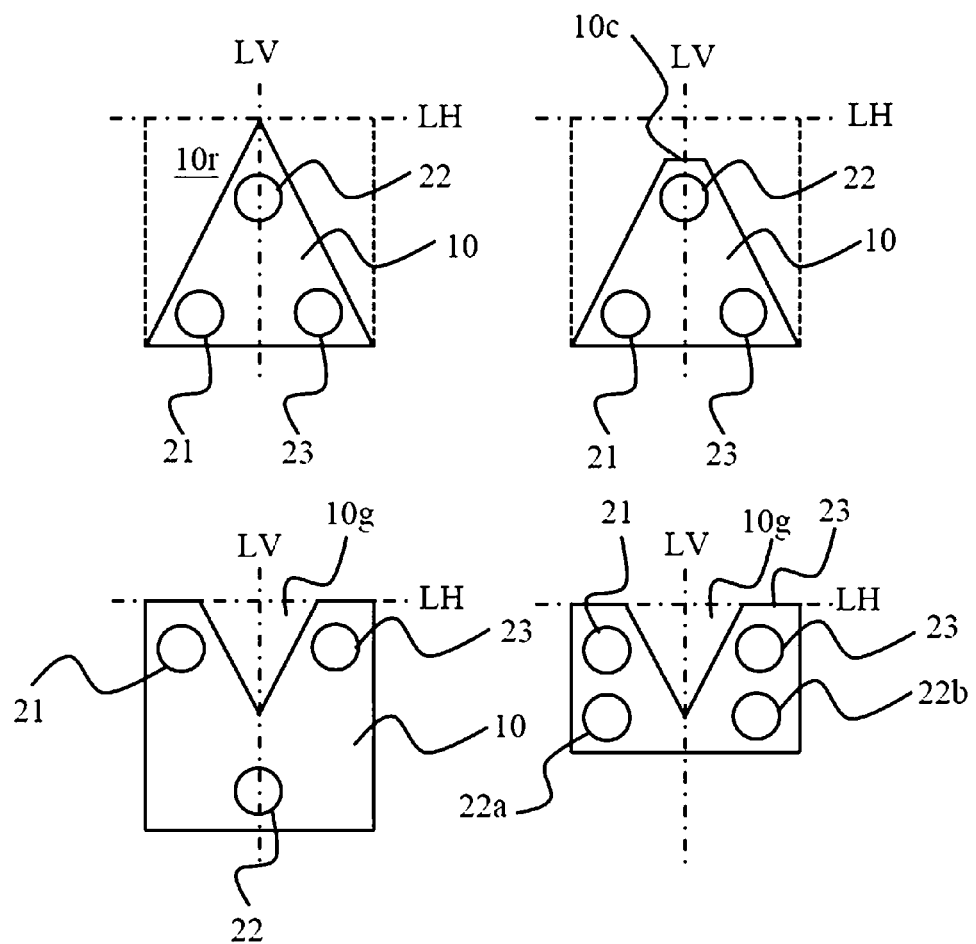
FIG. 6 illustrates diverse shapes of an end of the body according to the present disclosure.

FIG. 6 illustrates diverse shapes of an end of the body according to the present disclosure. Referring to (a), the first end 11 of the body 10 has a profile with at least a portion 10r of the body 10 being removed with respect to the horizontal line LH perpendicular to the length direction LV of the body 10, creating a convex upward profile in general. Referring to (b) as a preferred example, a portion above the opening 22 is cut off (e.g. into a flat top) to create a cut end part 10c, which allows to reduce a possible incidence of adjacent segment degeneration. Referring to (c) as another example, a groove 10g is formed in the first end 11 of the body 10 or a portion of the body 10 between the opening 21 and the opening 23 can be removed, creating an at least partially convex downward profile. Referring to (d) as yet another example, four openings 21, 22a, 22b, 23 may be formed in the first end, reducing the height of the body 10 and increasing fixation force at the same time, as compared with those of the example in (c). If the body 10 has a shape shown in (a) or (b), it is more preferable that those screws being inserted in the openings 21, 23 are directed towards the opening 22 such that the fixation force of the screws may be increased and a possible incidence of adjacent segment degeneration may be reduced.

Moreover, windows 40 are also provided. For the screws 20, fixed screws (e.g. the insertion angles of these screws are affected by the orientation of the openings 30) as well as variable screws (e.g. the insertion angles of these screws are not affected by the orientation of the openings 30) can be used, and the screws 20 used may have different lengths.

Figure 7:
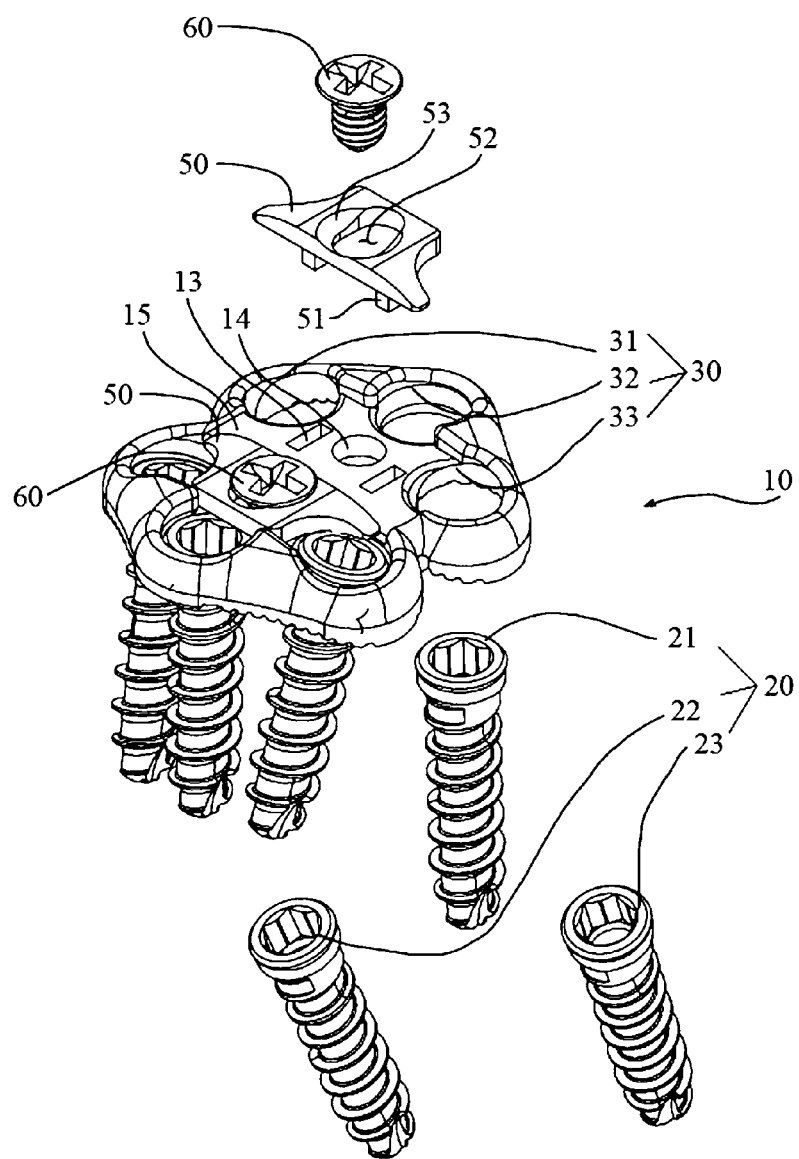
FIG. 7 through FIG. 9 illustrate another exemplary embodiment of the cervical vertebra fixation device according to the present disclosure.
Figure 8:
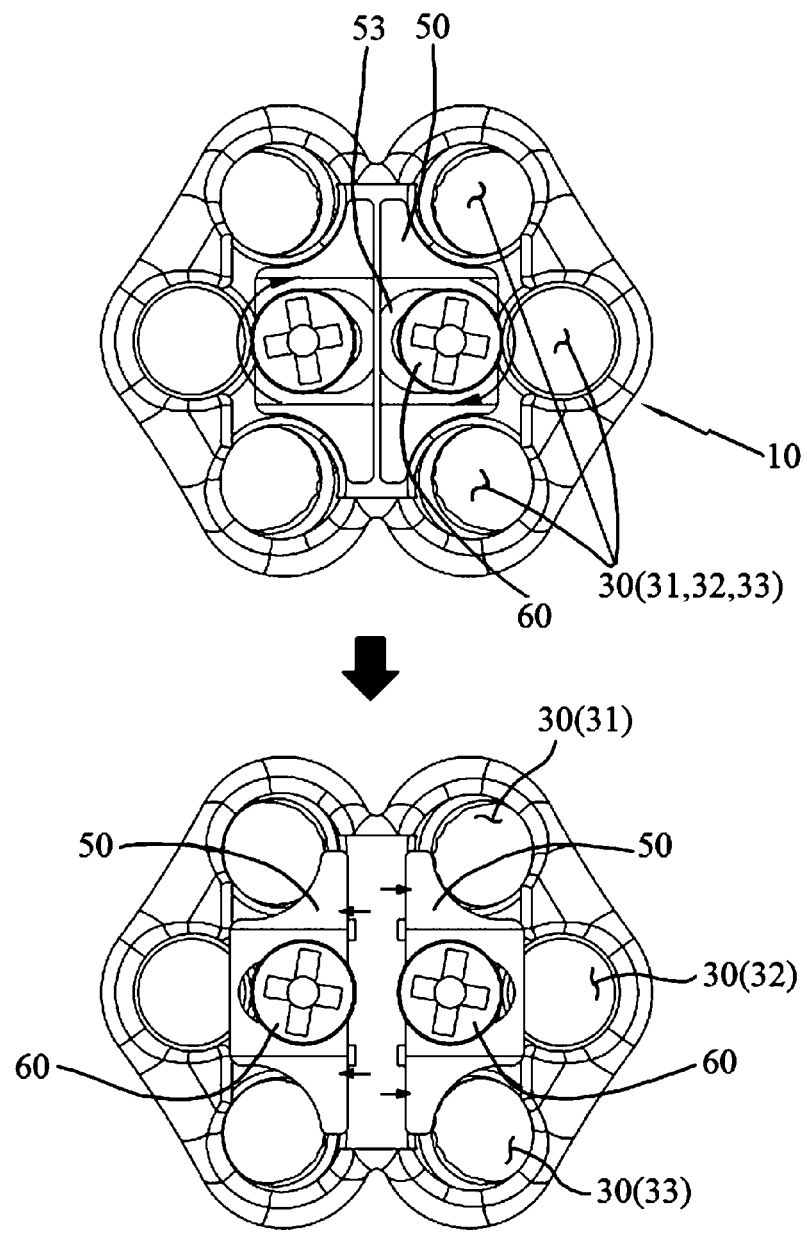
Figure 9:
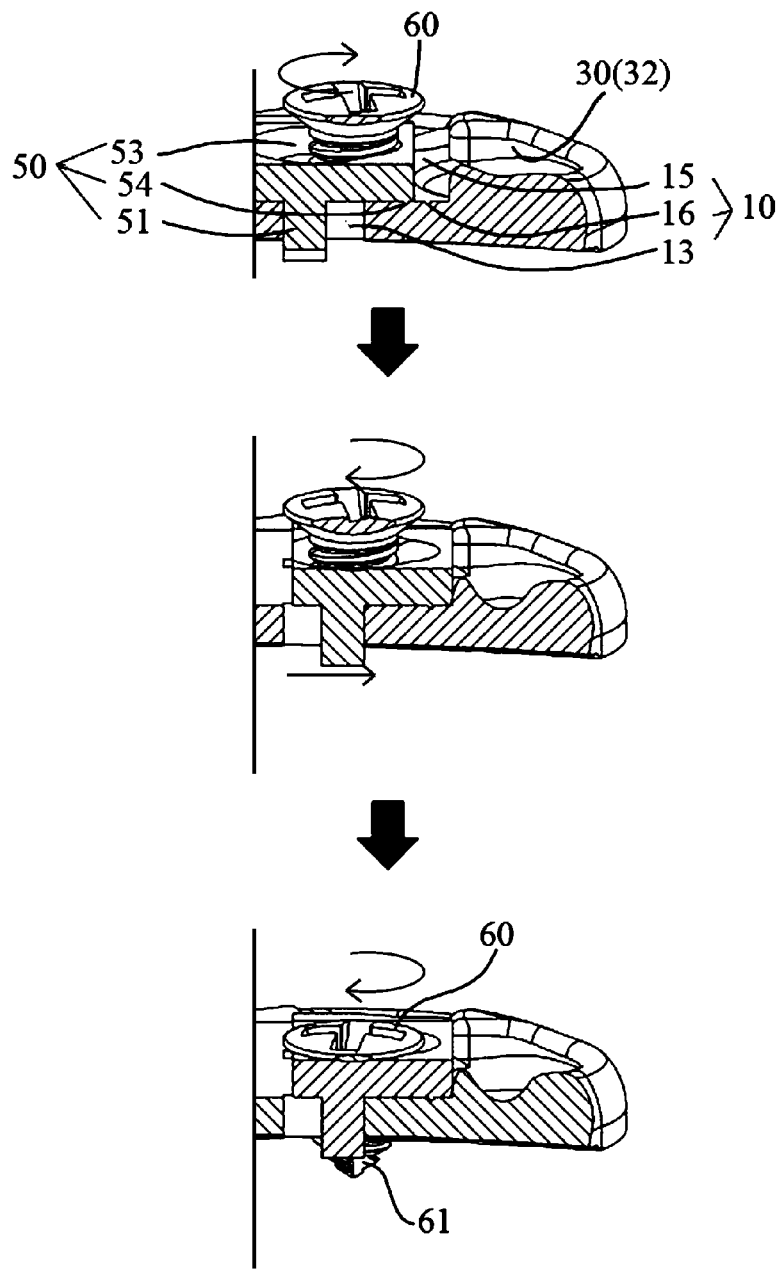
Figure 10:
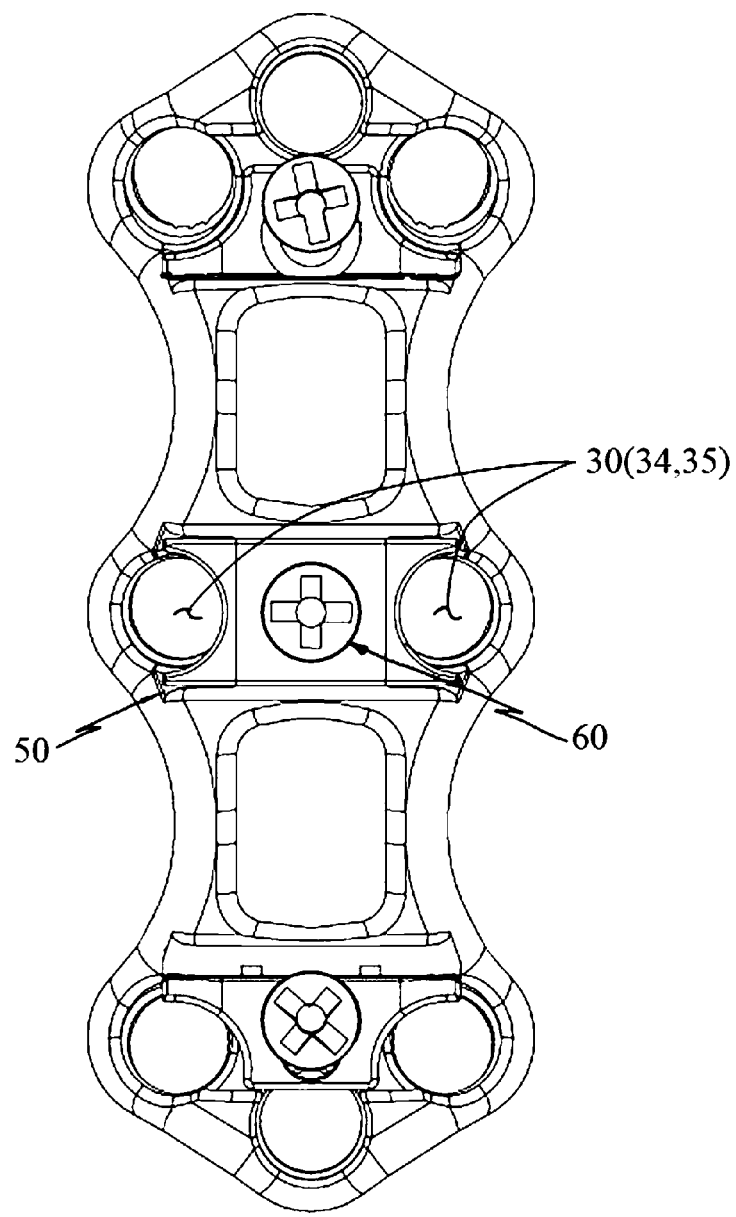
FIG. 10 through FIG. 14 illustrate yet another exemplary embodiment of the cervical vertebra fixation device according to the present disclosure.

FIG. 7 through FIG. 9 illustrate another exemplary embodiment of the cervical vertebra fixation device according to the present disclosure. The cervical vertebra fixation device includes a body 10, openings 30; 31, 32, 33, screws 20; 21, 22, 23, a cover 50 for preventing the escape of the screws, and a cover screw 60. While the cover 50 is coupled to the body 10, the cover 50 is movable with respect to the body 10 to allow the insertion of the screws 20; 21, 22, 23. In the embodiment shown in FIG. 7, the cover 50 has guide lugs 51 that are inserted and movable in corresponding guide grooves 13 formed in the body 10. The cover 50 is provided with a screw interlocking part 53 that interlocks with the cover screw 60 as it is inserted and rotationally moves down into a hole 52, allowing the cover 50 to move. For instance, the screw interlocking part 53 may be a unidirectionally inclined face. As shown in FIG. 8, when the cover screw 60 is rotated, the cover 50 moves into the openings 30; 31, 32, 33 and at least partially covers the openings 30; 31, 32, 33 such that the screws inserted into the openings 30; 31, 32, 33 are prevented from escaping therefrom. With this structure, it is possible to insert the screws when the cover 50 is coupled to the body 10, and to prevent the escape of the screws. The cover 50 is designed to partially cover the openings 30; 31, 32, 33 and thus, it can efficiently move in the cervical vertebra fixation device having a limited space. Preferably, the body 10 has a receiving groove 15 for receiving and/or guiding the cover 50. The presence of the receiving groove 15 makes it possible lower the total height of the cervical vertebra fixation device within the limited space, and if needed, the cover 50 can be guided in the receiving groove 15 in a stable manner. The height of the receiving groove 15 is not particularly limited as long as the receiving groove is designed to serve its role as described above. Moreover, the receiving groove 15 is formed in such a manner that it is extended to at least one of the openings 30; 31, 32, 33 (e.g. the bottom of the receiving groove 15 and the top face of the corresponding opening 30; 31, 32, 33 are connected continuously), allowing for easy covering of the openings 30; 31, 32, 33 with the cover 50. A hole 14 is provided in the body 10 for the cover screw 60 to be able to pass through. As shown in FIG. 9, a groove 16 formed in the body 10 and a projection 54 formed on the cover 50 work together for fixation, ensuring the connection between the two in a locked state. The cover screw 60 has a length long enough to run through the body 10 in the locked state, and an end 61 of the covering screw 60 reaches the bone. As a result, the fixation force of the cervical vertebra fixation device can be increased even more.

Figure 11:
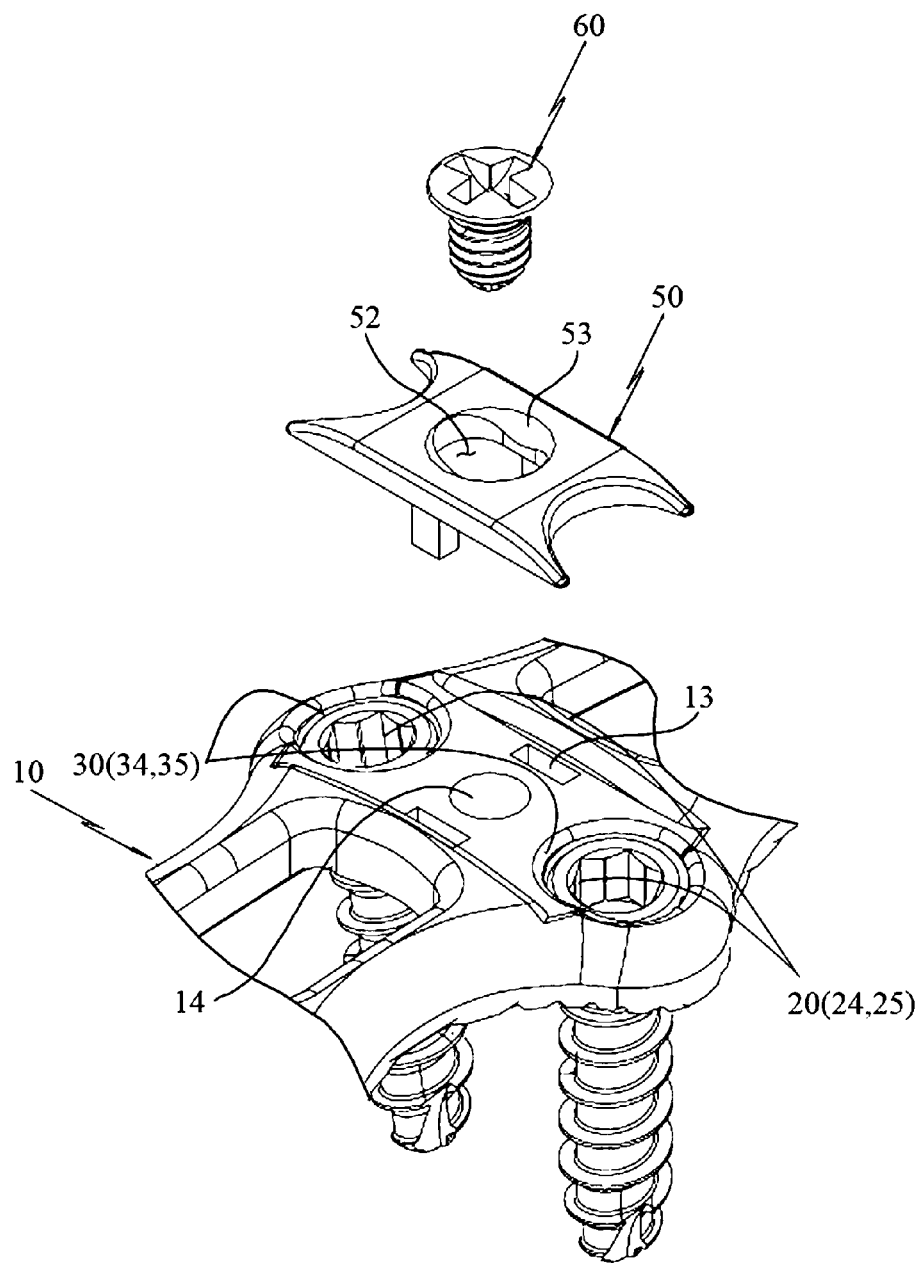
Figure 12:
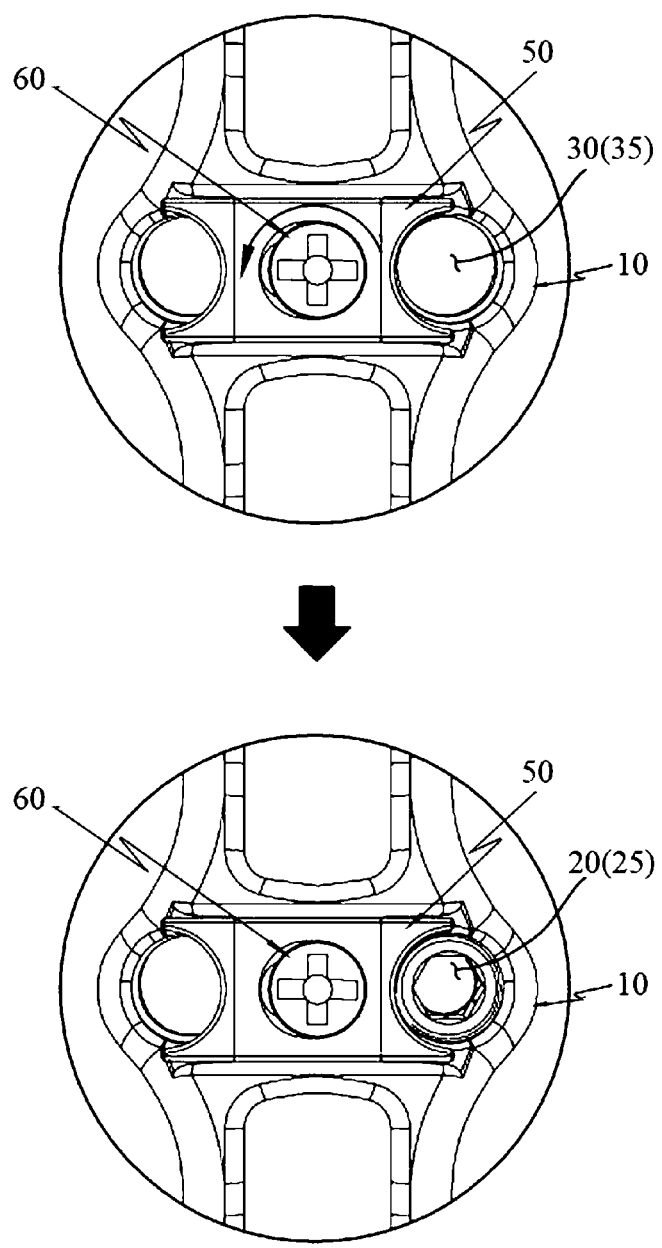
Figure 13:
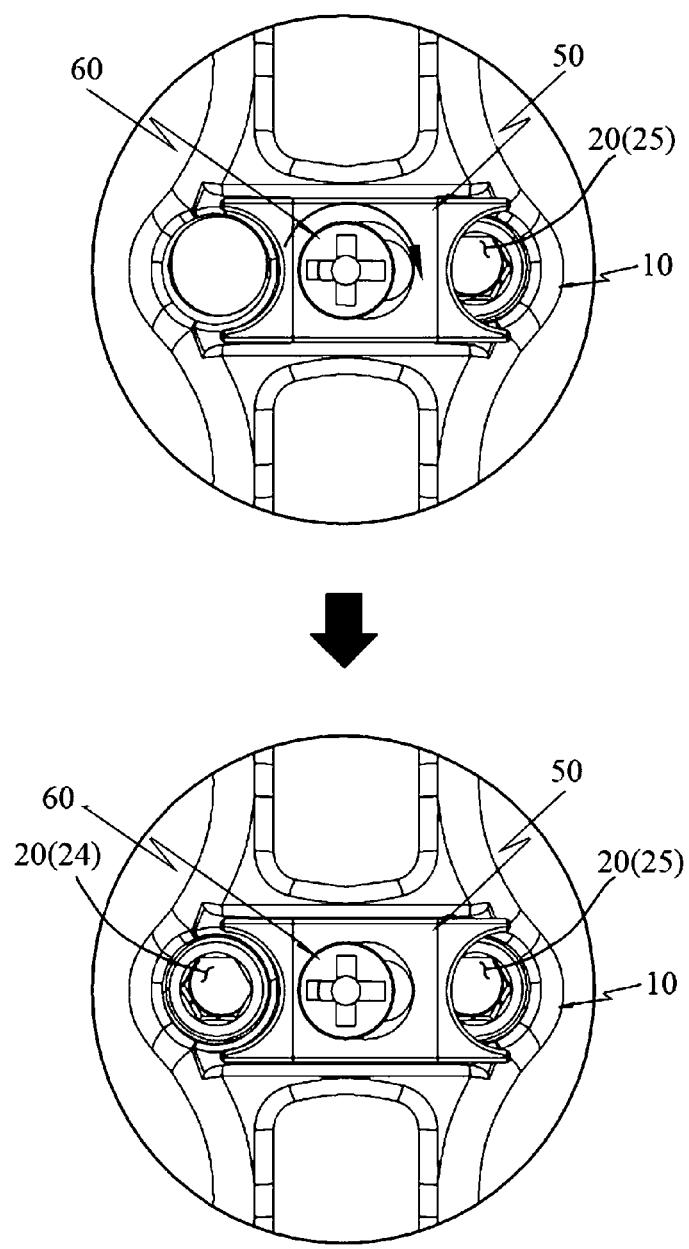
Figure 14:
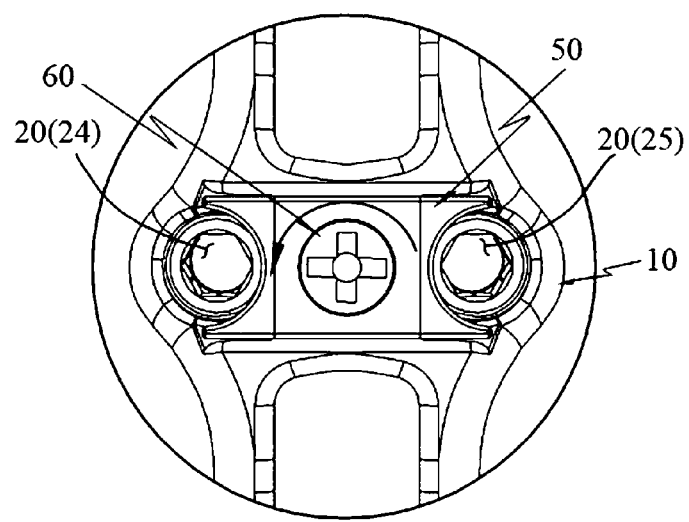

FIG. 10 through FIG. 14 illustrate yet another exemplary embodiment of the cervical vertebra fixation device according to the present disclosure. The cervical vertebra fixation device includes a cover 50 interlocking with openings 30, 34, 35, and a cover screw 60. Referring to FIG. 11, the body 10 has a guide groove 13 and a hold 14, and the cover 50 has a hole 52 and a screw interlocking part 53 that interlocks with the cover screw 60. The screw interlocking part 53 can be inclined in either direction (i.e. slanted sides with a lower center) in such a way that the cover 50 is able to move towards the opening 34 and the opening 35 to allow the insertion of the screws 20; 24, 25 into the openings 30; 34, 35 and to prevent the escape of the screws 20; 24, 25 from the openings 30; 34, 35. The screw 25 is inserted during the state where the cover 50 is being used in a way that the opening 35 is exposed (the state where the cover screw 60 is turned to one direction), as shown in FIG. 12. Then the cover 50 is moved to the opposite side (by turning the cover screw 60 to the other direction), and the screw 24 is inserted, as shown in FIG. 13. Next, the cover screw 60 is again turned all the way to the opposite direction, and the cover 50 moves to the position to be able to prevent the escape of both screws 20; 24, 25, as shown in FIG. 14.

The following describes various exemplary embodiments of the present disclosure.

(1) A cervical vertebra fixation device using a plurality of screws characterized by comprising: a body having a length extending across at least two bones, and including a first end and a second end opposite to the first end; and three or more openings formed in the body for receiving the plurality of screws, wherein the first end has a profile with at least a portion of the body being removed with respect to the horizontal line perpendicular to the length direction to prevent adjacent segment degeneration. The second end side may have a form identical with or different from that of the first end side.

(2) The cervical vertebra fixation device using a plurality of screws characterized in that the profile is a convex upward profile. Preferably, a profile between the openings may have an inwardly concave line inside the body.

(3) The cervical vertebra fixation device using a plurality of screws characterized in that at least part of the profile has an at least partially convex downward line.

(4) The cervical vertebra fixation device using a plurality of screws characterized in that the profile has a convex downward line with a groove between the openings.

(5) The cervical vertebra fixation device using a plurality of screws characterized by comprising four or more openings, with the openings being arranged either side of the groove.

(6) The cervical vertebra fixation device using a plurality of screws characterized in that at least one of three or more openings is formed in the body in such a manner that a screw is inserted therein at an angle.

(7) The cervical vertebra fixation device using a plurality of screws characterized in that the three or more openings are formed in the body in such a manner that a plurality of screws are inserted therein, respectively, facing each other.

(8) The cervical vertebra fixation device using a plurality of screws characterized by further comprising a cover for preventing the escape of the screws being inserted.

(9) The cervical vertebra fixation device using a plurality of screws characterized in that the cover is movable with respect to the body so as to allow the insertion of screws while the cover is coupled to the body.

(10) The cervical vertebra fixation device using a plurality of screws characterized in that the profile is formed of a convex upward line, and among the three or more openings in the body, one arranged near the first end is formed in such a manner that a screw is inserted therein at an angle.

(11) The cervical vertebra fixation device using a plurality of screws characterized in that the profile is formed of a convex upward line, and among the three or more openings, one is formed in a convex upward portion of the body and the other two are formed in the body in such a manner that screws are inserted therein respectively at an angle, facing towards the one formed in the convex upward portion of the body.

(12) The cervical vertebra fixation device using a plurality of screws characterized in that three openings are formed on the side of the first end, and the device further comprises screws to be inserted at an angle into the three openings, respectively, in which the screw inserted into the opening arranged at the closest to the first end and the other two screws inserted into their corresponding openings cross each other.

(13) The cervical vertebra fixation device using a plurality of screws characterized by further comprising variable screws to be inserted into three or more openings.

(14) A cervical vertebra fixation device using at least one screw, characterized by comprising: a body fixed into a bone; at least one opening formed in the body for receiving the at least one screw; a cover for preventing any escape of the screws inserted; and a cover screw, wherein the cover is movable with respect to the body to allow the insertion of screws while the cover is coupled to the body. As an alternative to those exemplary embodiments of the cervical vertebra fixation device having two openings and three openings, one or more openings can be present in the device.

(15) The cervical vertebra fixation device using a plurality of screws characterized in that the cover has a unidirectionally inclined face to interlock with the cover screw.

(16) The cervical vertebra fixation device using a plurality of screws characterized in that the cover has an inclined face on either direction to interlock with the cover screw.

(17) The cervical vertebra fixation device using a plurality of screws characterized in that the body has a receiving groove for receiving at least part of the cover.

(18) The cervical vertebra fixation device using a plurality of screws characterized in that the receiving groove is extended to at least one of the openings.

(19) The cervical vertebra fixation device using a plurality of screws characterized in that the cover screw has a length long enough to run through the body.

(20) The cervical vertebra fixation device using a plurality of screws characterized in that the cover has a shape for preventing any escape of the at least one opening.

(21) The cervical vertebra fixation device using a plurality of screws characterized in that the at least one opening comprises three or more openings, and the cover has a shape for preventing the escape of screws inserted into the three or more openings, respectively.

(22) The cervical vertebra fixation device using a plurality of screws characterized in that the at least one opening comprises three openings, and the cover has a shape for preventing the escape of screws inserted into the three openings, respectively.

(23) The cervical vertebra fixation device using a plurality of screws characterized in that the cover has a unidirectionally inclined face to interlock with the cover screw.

(24) The cervical vertebra fixation device using a plurality of screws characterized in that the profile is formed of a convex upward line, and among the three or more openings, one is formed in a convex upward portion of the body and the other two are formed in the body in such a manner that screws are inserted therein respectively at an angle, facing towards the one formed in the convex upward portion of the body.

What is claimed is:

1. A cervical vertebra fixation device using a plurality of screws and comprising a body having a length configured to extend across at least two bones, and including a first end and a second end opposite to the first end; characterized in including on each of the first and second ends:
   three or more openings formed in the body for receiving the plurality of screws,
   wherein a respective end has a profile with at least a portion of the body being removed with respect to a horizontal line perpendicular to a length direction of the body to prevent adjacent segment degeneration,
   wherein the profile is a convex upward profile,
   wherein among the three or more openings on each of the first and second ends, one opening is formed in a convex portion of the body and two other openings are formed in the body in such a manner that two screws are inserted therein respectively at an inclined angle, facing towards one screw inserted into the one opening formed in the convex portion of the body,
   wherein among the three or more openings on each of the first and second ends, the one opening is arranged closest to a respective end and is formed in such a manner that the one screw inserted into the one opening and the other two screws cross each other.

2. The cervical vertebra fixation device according to claim 1, further comprising a cover for preventing the screws inserted from escaping.

3. The cervical vertebra fixation device according to claim 2, wherein the cover is movable with respect to the body so as to allow the screws to be inserted while the cover is coupled to the body.

4. The cervical vertebra fixation device according to claim 1, further comprising variable screws to be inserted into three or more openings.

\* \* \* \* \*